United States Patent [19]

Supp

[11] 4,369,255

[45] Jan. 18, 1983

[54] METHOD OF OBTAINING IMPROVED EQUILIBRIUM CONDITIONS AND OF SIMULTANEOUSLY PRODUCING STEAM UNDER HIGH PRESSURE IN THE PRODUCTION OF METHANOL

[75] Inventor: Emil Supp, Dietzenbach, Fed. Rep. of Germany

[73] Assignee: Metallgesellschaft Aktiengesellschaft, Frankfurt am Main, Fed. Rep. of Germany

[21] Appl. No.: 287,007

[22] Filed: Jul. 27, 1981

[30] Foreign Application Priority Data

Jul. 29, 1980 [DE] Fed. Rep. of Germany ....... 3028646

[51] Int. Cl.$^3$ ...................... C07C 27/06; C07C 31/04
[52] U.S. Cl. .................................... 518/712; 518/713; 122/32; 122/488; 122/489; 165/134 R
[58] Field of Search .................. 518/712, 713; 122/32, 122/488, 489; 165/134 R

[56] References Cited

U.S. PATENT DOCUMENTS

| 4,074,660 | 2/1978 | Tsao ........................................ 122/32 |
| 4,263,141 | 4/1981 | Möller et al. ........................ 518/713 |

FOREIGN PATENT DOCUMENTS

| 680821 | 10/1952 | United Kingdom ................ 518/712 |
| 1316705 | 5/1973 | United Kingdom ................ 518/712 |
| 1364357 | 8/1974 | United Kingdom ................ 518/712 |

*Primary Examiner*—Howard T. Mars

*Attorney, Agent, or Firm*—Sprung, Horn, Kramer & Woods

[57] ABSTRACT

A method of controlling the equilibrium conditions and of simultaneously producing steam under high pressure in the production of methanol by a reaction of oxides of carbon and of hydrogen-containing gases at temperatures of 200° to 300° C. under a pressure of 20 to 100 bars at a copper-containing catalyst, which is contained within the reactor in tubes, which are indirectly cooled by boiling water under pressure, wherein the resulting steam is withdrawn together with circulating water and is separated from the water, the water is recycled and the evaporated water is replaced by feed water. According to the invention the process is carried out in such a manner that a perforated thin intermediate bottom plate is provided in the reactor spaced 20 to 150 cm over the lower tube plate, the reactor is fed with the circulating water above that intermediate bottom and with feed water below that intermediate bottom, the gaseous reaction mixture is cooled by 20° to 50° C. in the lower part of the catalyst-filled tubes in a tube length of 20 to 150 cm, the feed water is heated in the reactor to temperatures of 230° to 290° C. with evaporation of part of the feed water, the resulting mixture of steam and circulating water is separated, the circulating water is recycled and the resulting high-pressure steam is withdrawn. In this method, steam under a pressure above 60 bars can be produced whereas only a pressure of 40 bars has been reached heretofore.

7 Claims, 1 Drawing Figure

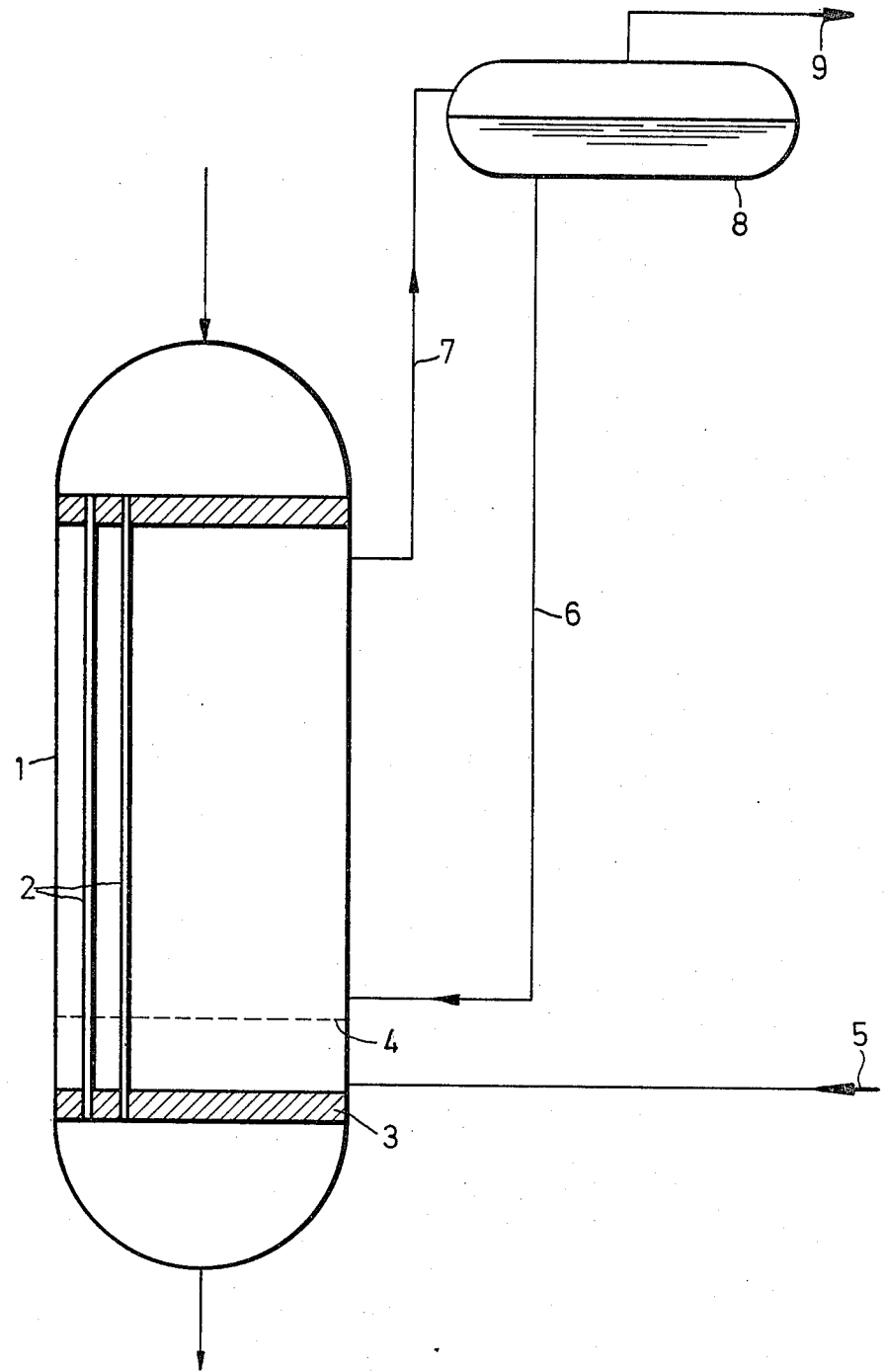

METHOD OF OBTAINING IMPROVED EQUILIBRIUM CONDITIONS AND OF SIMULTANEOUSLY PRODUCING STEAM UNDER HIGH PRESSURE IN THE PRODUCTION OF METHANOL

BACKGROUND OF THE INVENTION

1. Field of the Invention

This invention relates to a method of obtaining improved equilibrium conditions and of simultaneously producing steam under high pressure in the production of methanol by a reaction of oxides of carbon and of hydrogen-containing gases at temperatures of 200° to 300° C. under a pressure of 20 to 100 bars in the presence of a copper-containing catalyst, contained within a reactor in tubes, indirectly cooled by boiling water under pressure, wherein the resulting steam is withdrawn together with circulating water and is separated from the water, the water is recycled and the evaporated water is replaced by feed water.

2. Discussion of Prior Art

It is known to produce synthesis gas containing hydrogen and oxides of carbon by cracking hydrocarbons with steam at temperatures above 700° C. in the presence of an indirectly heated, nickel-containing catalyst. It is further known to form methanol by reacting the synthesis gas under pressures of 30 to 80 at temperatures of 230° to 280° C. in the presence of a copper-containing catalyst, contained in a reactor in tubes which are indirectly cooled with water. It is also known to utilize the cooling of the reactor tubes for production of high-pressure steam (German Pat. No. 20 13 297).

A known apparatus for producing methanol in another process comprises a tubular reactor having tubes contacted by flowing boiling water under pressure. In that apparatus, the feed water enters the lower part of the reactor and the resulting stream is fed to a superheater. Part of that steam can be withdrawn as high-pressure steam and another part can be supplied to a turbine, which drives a compressor. The remaining part of the steam can be recovered as turbine steam (German Pat. No. 21 23 950).

In the operation of the previously known tubular reactor, circulating water from a steam header is fed to the tubular reactor. Part of the fed water is evaporated at the catalyst-filled tubes, in which the components $H_2O$, $CO$ and $CO_2$ are reacted to form methanol. By thermosiphon action, the resulting steam together with circulating water is forced into the steam header, where the steam is separated whereas the water, which is at its boiling point is returned to the lower part of the reactor. The steam withdrawn from the steam header must be returned to the system as feed water. Depending on the preheating of that feed water the temperature in the steam header will be more or less close to the boiling point of water. If the water is circulated about ten times, feed water is fed at a temperature of 120° C. and a pressure of 40 bars is maintained in the system, the circulating water fed to to the lower part of the reactor will be at a temperature of about 237° C., which is 13° C. under its boiling point. As a result, the temperature difference at the lower part of the reactor tubes containing catalyst at a temperature of about 255° C. is very low and precludes an appreciable heat exchange and a cooling of the reacting mixed gases in the tubes.

Only steam at a pressure up to about 40 bars can be produced in the known tubular reactors for producing methanol because the copper catalyst is susceptible to elevated temperatures and a good equilibrium control is desired.

It is an object of the invention to avoid these disadvantages of the state of the art and to obtain a higher temperature difference in the lower part of the reactor and to effect an improved and more intense cooling of the reacting mixed gases. The equilibrium control is to be improved and steam under higher pressure is to be produced at the same time. The process should involve lower energy costs.

This object is accomplished according to the invention in that a perforated thin intermediate bottom plate is provided, which is spaced 20 to 150 cm over the lower tube plate, the reactor is fed with the circulating water above that intermediate bottom and with the feed water below that intermediate bottom, the gaseous reaction mixture is cooled by 20° to 50° C. in the lower part of the catalyst-filled tubes in a tube length of 20 to 150 cm, the feed water is heated in the reactor to temperatures of 230° to 290° C. with evaporation of part of the feed water, the resulting mixture of steam and circulating water is separated, the circulating water is recycled and the resulting high-pressure steam is withdrawn.

In accordance with the invention the intermediate bottom is suitably spaced 50 cm over the lower tube plate.

The circulating water fed to the reactor is desirably at a temperature of 200° to 300° C., preferably at a temperature of 230° to 290° C., and the feed water is fed at a temperature of 100° to 180° C., preferably 110° to 150° C.

The advantages afforded by the invention reside particularly in that the temperature difference between the cooling fluid and the catalyst contained in the tubes can be increased in the lower part of the reactor in a simple, energy-saving process. As a result, the heat exchange is increased and the reacting gas mixture is cooled to a lower temperature so that the thermodynamic equilibrium is promoted. The temperatures used are within the limits determined by the recrystallizating characteristics of the catalyst. Methanol can be produced more economically in accordance with the invention.

BRIEF DESCRIPTION OF DRAWING

The invention is shown diagrammatically and by way of example in the drawing and will now be described more in detail;

The drawing shows the reactor 1, catalyst tubes 2, the lower tube plate 3, the intermediate bottom plate 4, a feeding of feed water at 5, a feeding of circulating water at 6, a mixture of steam and circulating water at 7, a separation of steam from the circulating water in the steam header at 8 and a withdrawal of high-pressure steam at 9.

EXAMPLE

A reactor 1 for producing methanol contains tubes 2, which contain the catalyst. An intermediate bottom plate 4 is spaced 50 cm above the lower tube plate 3 and may consist of a thin sheet steel which has apertures consisting of bores small in diameter. The feed water at a temperature of 120° C. is introduced into the reactor through a supply conduit 5 closely above the lower tube plate 3. That unmixed feed water contacts the lower part of the catalyst tubes 2 and cools the reacting mixed gases by 35° C. in a pipe length of 50 cm. As a result, the feed water is heated to 280° C. and a small part of it is evaporated.

Circulating water at a temperature of 280° C. is introduced through a conduit 6 into the reactor 1 closely above the intermediate bottom plate 4. The colder feed water 5 fed below the intermediate bottom plate 4 is uniformly distributed by the latter whereas on the other side a backmixing with the hotter circulating water fed above the intermediate bottom plate 4 is prevented.

The feed water 5 is mixed with the circulating water 6 only above the intermediate bottom plate 4. As a result, that portion of the catalyst tubes 2 which is disposed above the intermediate bottom plate 4 is operated at a temperature of 280° C. so that a pressure of more than 60 bars is obtained in the water-circulating system whereas only pressures up to 40 bars can be obtained in the previous processes. When the mixture of water vapor and circulating water has been withdrawn at 7 and has been separated into its two components at 8, high-pressure steam under a pressure in excesss of 60 bars is recovered at 9 and can be used for numerous purposes in the same plant, e.g., for expansion with performance of work, for instance, in condensing steam turbines, or for a generation of electric power by driving gas compressors, or for supplying the energy required for the final distillation of the methanol, or for other purposes. Owing to the considerable advantages by the process as regards energy consumption, the process is particularly economical.

What is claimed is:

1. In a method of producing methanol by reaction of an oxide of carbon and hydrogen at a temperature of 200° to 300° C. under a pressure of 20 to 100 bars by passing said oxide of carbon and hydrogen through at least one tube containing a copper-containing catalyst, which tube is disposed on a lower tube plate and is housed in a reactor through which passes circulating boiling water under pressure to indirectly cool the contents of said tube, steam resulting therefrom is withdrawn together with the circulating water and is separated therefrom the improvement for improving the equilibrium within the reactor and simultaneously producing high pressure steam, which comprises disposing an intermediate bottom plate 20 to 150 cm over said lower tube plate, whereby to define a lower cooling zone and an upper cooling zone, said intermediate bottom plate provided with apertures to convey water from said lower cooling zone to said upper cooling zone, feeding circulating water above said intermediate bottom plate and feed water below said intermediate bottom plate, whereby the gaseous reaction mixture within said tube is cooled by 20° to 50° C. in the lower part of the catalyst-filled tube in the tube length of 20 to 150 cm, the feed water is heated in the reactor to a temperature of 230° to 290° C. with evaporation of a portion of the feed water, the resulting mixture of steam and circulating water is separated, the circulating water is recycled and the resulting high-pressure steam is withdrawn.

2. A method according to claim 1, wherein the intermediate bottom plate is spaced 50 cm over the lower tube plate.

3. A process according to claim 1, wherein the circulating water is fed at a temperature of 200° to 300° C.

4. A process according to claim 1, wherein the circulating water is fed at a temperature of 230° to 290° C.

5. A process according to claim 1, wherein the feed water is fed at a temperature of 100° to 180° C.

6. A process according to claim 1, wherein the feed water is supplied at a temperature of 110° to 150° C.

7. A process according to claim 1, wherein said intermediate bottom plate has apertures therein in the form of bores.

* * * * *